United States Patent
Beight et al.

(10) Patent No.: US 6,586,459 B2
(45) Date of Patent: Jul. 1, 2003

(54) ANTITHROMBOTIC AGENTS

(76) Inventors: Douglas Wade Beight, 9368 Benchmark Dr., Apartment G, Indianapolis, IN (US) 46240; Trelia Joyce Craft, 10404 E. 46th St., Indianapolis, IN (US) 46236; Jeffry Bernard Franciskovich, 5036 Quail Ridge La., Indianapolis, IN (US) 46254; Theodore Goodson, Junior, 4045 Devon Dr., Indianapolis, IN (US) 46226; Steven Edward Hall, 102 Nuttal Pl., Chapel Hill, NC (US) 27514; David Kent Herron, 5945 Andover Rd., Indianapolis, IN (US) 46220; Valentine Joseph Klimkowski, 4504 Camelot La., Carmel, IN (US) 46033; Jeffrey Alan Kyle, 10434 Collingswood Land, Fishers, IN (US) 46038; John Joseph Masters, 12047 Flint Stone Ct., Fishers, IN (US) 46038; David Mendel, 11348 Woods Bay La., Indianapolis, IN (US) 46236; Guy Milot, 406 Parkview Crescent, Chapel Hill, NC (US) 27516; Jason Scott Sawyer, 5718 N. Winthrop Ave., Indianapolis, IN (US) 46220; Robert Theodore Shuman, 180 Barcelona Rd., Sedona, AZ (US) 86336; Gerald Floyd Smith, 825 Queenswood Ct., Indianapolis, IN (US) 46217; Anne Louise Tebbe, 6202 N. Sherman Dr., Indianapolis, IN (US) 46220; Jennifer Marie Tinsley, 4542 State Rd. 39 North, Martinsville, IN (US) 46151; Leonard Crayton Weir, 6520 Englehardt Dr., Raleigh, NC (US) 27613; James Howard Wikel, 4068 Sunshine Way, Greenwood, IN (US) 46142; Michael Robert Wiley, 7725 Langwood Dr., Indianapolis, IN (US) 46268; Ying Kwong Yee, 5127 Briarstone Trace, Carmel, IN (US) 46033

( * ) Notice: Subject to any disclaimer, the term of this patent is extended or adjusted under 35 U.S.C. 154(b) by 0 days.

(21) Appl. No.: 09/967,203

(22) Filed: Sep. 28, 2001

(65) Prior Publication Data

US 2002/0049234 A1 Apr. 25, 2002

Related U.S. Application Data

(62) Division of application No. 09/445,973, filed on Mar. 31, 2000, now Pat. No. 6,313,151.
(60) Provisional application No. 60/050,881, filed on Jun. 26, 1997.

(51) Int. Cl.[7] .............. A61K 31/404; A61K 31/44; A61K 31/381; C07D 209/40; C07D 213/82; C07D 333/36; A61P 7/02

(52) U.S. Cl. ............. 514/419; 514/255.06; 514/256; 514/275; 514/352; 514/447; 544/325; 544/358; 544/407; 546/265; 546/308; 548/483; 549/69

(58) Field of Search .................. 548/483; 549/69; 546/265, 308; 544/325, 358, 407; 514/447, 352, 419, 255.06, 275, 256

(56) References Cited

U.S. PATENT DOCUMENTS

| | | |
|---|---|---|
| 5,492,895 A | 2/1996 | Vlasuk et al. |
| 5,518,735 A | 5/1996 | Sturzebecher et al. |
| 5,721,214 A | 2/1998 | Marlowe et al. |
| 6,140,351 A * | 10/2000 | Arnaiz .................. 514/336 |

FOREIGN PATENT DOCUMENTS

| | | |
|---|---|---|
| EP | 024 290 | 7/1980 |
| WO | 08/994284 | 12/1997 |
| WO | 09/187459 | 11/1998 |
| WO | WO 99/00121 | 1/1999 |
| WO | WO 99/00127 | 1/1999 |
| WO | WO 99/00128 | 1/1999 |
| WO | WO 99/32477 | 7/1999 |
| WO | WO 99/42439 | 8/1999 |
| WO | WO 00/39092 | 7/2000 |
| WO | WO 00/39111 | 7/2000 |
| WO | WO 00/39117 | 7/2000 |
| WO | WO 00/39118 | 7/2000 |

OTHER PUBLICATIONS

Liu KC and Shih BJ. T'ai–wan Yao Hsueh Tsa Chih (1983), 35(1), 102–4.*

U.S. patent application Ser. No. 08/994,284, filed Dec. 1997, Priority for WO99/32477.

U.S. patent application Ser. No. 09/187,459, filed Nov. 1998, Priority for WO99/32477.

Uchida, H., et al. Reactions of N–Acylaminoacetamidine with 1,3–Bifunctional Compounds. Bulletin of the Chemical Society of Japan, vol. 46, 3277–3280 (1973), pp. 3277–3280.

Wallis, R.B. Inhibitors of Coagulation Factor Xa: From Macromolecular Beginnings to Small Molecules. Current Opinion in Therapeutic Patents. 1993, vol. 3, No. 8, pp. 1173–1179.

Chem. Abstr., vol. 99, No. 23, Dec. 5, 1993 (Columbus,OH, USA) p. 743, col. 2, the abstract No. 194839t, and full paper Liu et al. "Potential antineoplastic sulfhydryl agents. IV. Synthesis of N1–phenylindole–2,3 dicarboxamide." Tai-–wan Yao Hsueh Tsa Chih. Journal of the Taiwan Pharmaceutical Association, vol. 35, No. 1 (1983), pp. 102–104 (Eng).

(List continued on next page.)

*Primary Examiner*—Evelyn Mei Huang

(57) ABSTRACT

This application relates to a compound of formula I (or a prodrug thereof or a pharmaceutically acceptable salt of the compound or prodrug thereof) as defined herein, pharmaceutical compositions thereof, and its use as an inhibitor of factor Xa, as well as a process for its preparation and intermediates therefor.

12 Claims, No Drawings

OTHER PUBLICATIONS

Chem. Abstr., vol. 118, No. 9, Mar. 1, 1993 (Columbus, OH, USA), p. 824, col. 1, the abstract No. 80809p, Ishikawa et al, "Preparation of 2–acylpyridine derivatives as agrochemical fungicides." Jpn. Kokai Tokkyo Koho JP 04,187,675, Jul. 6, 1992.

Edmunds, Jeremy J. and Rapundalo, Stephen T., (Doherty, Annette M. Section Editor), Annual Reports in Medicinal Chemistry, (1996), 31, 51–60.

Myers, H. V., et al., Molecular Diversity, (1995), 1, 13–20.

Journal of the Chemical Society, GB, Chemical Society. Letchworth, Aug. 1, 1965, XP002055390, "Pyrido (3,2–d)pyrimidin–4(3H)–ones." Irwin, W. J., et al., pp. 4240–4246.

Current Pharmaceutical Design, 1996, 2., "Factor Xa Inhibitors," Kunitada, Satoshi, et al., pp. 531–542.

Kaiser B and Hauptmann J. Cardiovascular Drug Reviews. 12 (3), 1994, pp. 225–236.

* cited by examiner

ANTITHROMBOTIC AGENTS

This application is a divisional of copending application Ser. No. 09/445,973, filed Mar. 31, 2000 (PCT/US98/13384, international filing date Jun. 26, 1998), now U.S. Pat. No. 6,313,151 B1, the entire disclosure of which herein is incorporated by reference, and claims the benefit of U.S. Provisional Application No. 60/050,881, filed Jun. 26, 1997.

This invention relates to antithrombotic heterocycles which demonstrate activity as inhibitors of factor Xa and, accordingly, which are useful anticoagulants in mammals. In particular it relates to heterocycles having high anticoagulant activity, and antithrombotic activity. Thus, this invention relates to new inhibitors of factor Xa, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Jeremy J. Edmunds and Stephen T. Rapundalo (Annette N. Doherty, Section Editor), *Annual Reports in Medicinal Chemistry*, (1996), 31, 51–60.

Although the heparins and coumarins are effective anticoagulants, no commercial drug has yet emerged from the small synthetic molecules; and despite the continuing promise for this class of compounds, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain homeostasis.

The present invention is directed to the discovery that the compounds of the present invention, as defined below, are potent inhibitors of factor Xa which may have high bio-availability following oral administration.

According to the invention there is provided a method of inhibiting factor Xa comprising using an effective amount of a factor Xa inhibiting compound of formula I

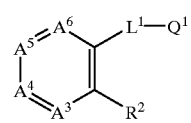

wherein $A^3$, $A^4$, $A^5$ and $A^6$, together with the two carbons to which they are attached, complete a substituted heteroaromatic ring in which (a) one of $A^3$, $A^4$, $A^5$ and $A^6$ is N, and each of the others is $CR^3$, $CR^4$, $CR^5$ or $CR^6$, respectively;

(b) two adjacent residues of $A^3$, $A^4$, $A^5$ and $A^6$ together form S, and each of the others is $CR^3$, $CR^4$, $CR^5$ or $CR^6$, respectively;

(c) two non-adjacent residues of $A^3$, $A^4$, $A^5$ and $A^6$ are each N, and each of the others is $CR^3$, $CR^4$, $CR^5$ or $CR^6$, respectively; or (d) $A^3$ and $A^4$ together form a fused benz ring, and $A^5$ and $A^6$ together form —NH—;

wherein each of $R^3$, $R^4$, $R^5$ and $R^6$ is hydrogen, or one or two of $R^3$, $R^4$, $R^5$ and $R^6$ is independently chloro, bromo or methyl and the others are hydrogen;

$L^1$ is —NH—CO— or —CO—NH— such that —$L^1$—$Q^1$ is —NH—CO—$Q^1$ or —CO—NH—$Q^1$;

$Q^1$ is phenyl, 2-furanyl, 2-thienyl, 4-thiazolyl, 2-pyridyl, 2-naphthyl, 1,2-dihydrobenzofuran-5-yl, 1,2-dihydrobenzofuran-6-yl or 1,2-benzisoxazol-6-yl in which the phenyl may bear a 2-fluoro substituent or may bear one, two or three substituents at the 3-, 4- or 5-position(s) independently selected from halo, cyano, carbamoyl, aminomethyl, methyl, methoxy, difluoromethoxy, hydroxymethyl, formyl, vinyl, amino, hydroxy and 3,4-methylenedioxy, the 2-furanyl or 2-thienyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position; or —CO—$Q^1$ is cyclopentenylcarbonyl or cyclohexenylcarbonyl;

$R^2$ is —$L^{2A}$—$Q^{2A}$, —$L^{2B}$—$Q^{2B}$, —$L^{2C}$—$Q^{2C}$ or —$L^{2D}$—$Q^{2D}$ wherein $L^{2A}$ is a direct bond; and $Q^{2A}$ is

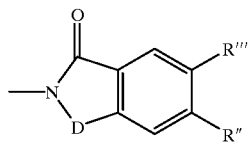

-continued

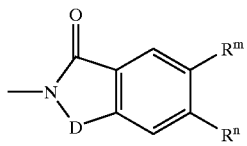

in which D is carbonyl or —CHR$^k$— in which R$^k$ is hydrogen, hydroxy, (1–6C)alkoxy or —CH$_2$—R$^j$ in which R$^j$ is carboxy, [(1–4C) alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

L$^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$—O—Q$^{2B}$ or —O—CH$_2$—Q$^{2B}$; and Q$^{2B}$ is

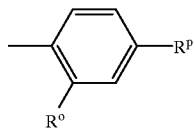

in which R$^o$ is hydrogen, halo, (1–6C)alkyl, (1–4C)alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxo, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl;

L$^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —L$^{2C}$—Q$^{2C}$ is —NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—, —NR$^w$—CH$_2$—, —O—, —O—CH$_2$— or —S—CH$_2$—; Y is —NR$^w$—CH$_2$— or —O—CH$_2$—; each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and Q$^{2C}$ is 1-(4-pyridyl)piperidin-4-yl, 1-(4-pyridyl)piperidin-3-yl or 1-(4-pyridyl)pyrrolidin-3-yl in which the pyridyl may bear a substituent at its 2-position selected from cyano, aminomethyl, carboxy, hydroxymethyl and (1–2C)alkyl;

L$^{2D}$ is —NH—CO— such that —L$^{2D}$—Q$^{2D}$ is —NH—CO—Q$^{2D}$; and

Q$^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl or 3,4-didehydropiperidin-4-yl (either one bearing a substituent at the 1-position selected from methylsulfonyl, phenylsulfonyl, (1–5C)alkyl, (4–7C)cycloalkyl, tetrahydropyran-4-yl, 4-thiacyclohexyl and —CH$_2$—R$^z$ in which R$^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent);

or a prodrug of the compound of formula I;

or a pharmaceutically acceptable salt of the compound of formula I or prodrug thereof.

A particular factor Xa inhibiting compound of formula I is one wherein

A$^3$, A$^4$, A$^5$ and A$^6$, together with the two carbons to which they are attached, complete a substituted heteroaromatic ring in which (a) one of A$^3$, A$^4$, A$^5$ and A$^6$ is N, and each of the others is CR$^3$, CR$^4$, CR$^5$ or CR$^6$, respectively;

(b) two adjacent residues of A$^3$, A$^4$, A$^5$ and A$^6$ together form S, and each of the others is CR$^3$, CR$^4$, CR$^5$ or CR$^6$, respectively;

(c) two non-adjacent residues of A$^3$, A$^4$, A$^5$ and A$^6$ are each N, and each of the others is CR$^3$, CR$^4$, CR$^5$ or CR$^6$, respectively; or (d) A$^3$ and A$^4$ together form a fused benz ring, and A$^5$ and A$^6$ together form —NH—; wherein each of R$^3$, R$^4$, R$^5$ and R$^6$ is hydrogen, or one or two of R$^3$, R$^4$, R$^5$ and R$^6$ is independently chloro, bromo or methyl and the others are hydrogen;

L$^1$ is —NH—CO— or —CO—NH— such that —L$^1$—Q$^1$ is —NH—CO—Q$^1$ or —CO—NH—Q$^1$;

Q$^1$ is phenyl, 2-thienyl, 4-thiazolyl, 2-pyridyl, 2-naphthyl or 1,2-benzisoxazol-6-yl in which the phenyl may bear one, two or three substituents at the 3-, 4- or 5-position(s) independently selected from halo, cyano, carbamoyl, aminomethyl, methyl, methoxy, hydroxymethyl, formyl, vinyl, amino, hydroxy and 3,4-methylenedioxy, the 2-thienyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position;

R$^2$ is —L$^{2A}$—Q$^{2A}$, —L$^{2B}$—Q$^{2B}$, —L$^{2C}$—Q$^{2C}$ or —L$^{2D}$—Q$^{2D}$ wherein L$^{2A}$ is a direct bond; and Q$^{2A}$ is

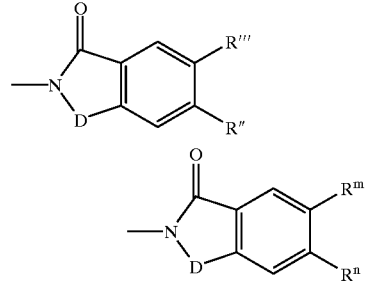

in which D is carbonyl or —CHR$^k$— in which R$^k$ is hydrogen, hydroxy, (1–6C)alkoxy or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

L$^{2B}$ is —NH—CO—, —O—CO—, —CH$_2$—O— or —O—CH$_2$— such that —L$^{2B}$—Q$^{2B}$ is —NH—CO—Q$^{2B}$, —O—CO—Q$^{2B}$, —CH$_2$—O—Q$^{2B}$ or —O—CH$_2$—Q$^{2B}$; and $Q^{2B}$ is

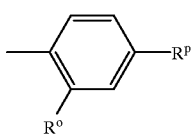

in which $R^o$ is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —S(O)$_q$— (wherein q is 0, 1 or 2), or —NR$^r$— (wherein $R^r$ is hydrogen or methyl); and $R^q$ is (1–6C)alkyl, phenyl, 3-pyridyl or 4-pyridyl;

$L^{2C}$ is —NR$^v$—CO—X—, —NR$^v$—CS—Y—, —CH$_2$—CO—NR$^w$—CH$_2$—, —O——CO—, —O—CH$_2$—, —S—CH$_2$— or —CH$_2$—NR$^x$—CH$_2$— such that —L$^{2C}$—Q$^{2C}$ is —NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—CH$_2$—, —O—CH$_2$— or —S—CH$_2$—; Y is —NR$^w$—CH$_2$— or —O—CH$_2$—; each of $R^v$ and $R^w$ is independently hydrogen, benzyl or (1–6C)alkyl which is not branched at the α-position; and $R^x$ is hydrogen, benzyloxycarbonyl or [(1–4C)alkoxy]carbonyl; and $Q^{2C}$ is 1-(4-pyridyl)piperidin-4-yl in which the pyridyl may bear a substituent at its 2-position selected from cyano, aminomethyl, carboxy, hydroxymethyl and (1–2C)alkyl;

$L^{2D}$ is —NH—CO— such that —L$^{2D}$—Q$^{2D}$ is —NH—CO—Q$^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —CH$_2$—$R^z$ in which $R^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent;

or a prodrug of the compound of formula I;

or a pharmaceutically acceptable salt of the compound of formula I or prodrug thereof.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In general, the factor Xa inhibiting compounds of formula I are believed to be novel and, thus, to constitute an additional aspect of the invention. Thus, according to the invention there is provided a novel compound of formula I (or a pharmaceutically acceptable salt thereof) according to any of the definitions herein of a compound of formula I, provided that the compound is not one which is not novel.

A pharmaceutically acceptable salt of an antithrombotic agent of the instant invention includes one which is an acid-addition salt made from a basic compound of formula I and an acid which provides a pharmaceutically acceptable anion, as well as a salt which is made from an acidic compound of formula I and a base which provides a pharmaceutically acceptable cation. Thus, a salt of a novel compound of formula I as provided herein made with an acid or base which affords a pharmaceutically acceptable counterion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted. When two adjacent residues form a (fused) benz ring, they form a cis,cis-buta-1,3-dien-1,4-diyl divalent radical.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–2C)alkyl is methyl or ethyl, and more particularly is methyl; for (1–4C)alkyl is methyl, ethyl, propyl, isopropyl, butyl, isobutyl, or t-butyl, and more particularly is methyl, isopropyl, butyl or t-butyl; for (1–6C)alkyl is methyl, ethyl, propyl, butyl, pentyl or hexyl, and more particularly is methyl, butyl or hexyl. A particular value for halo is bromo or chloro, and more particularly is chloro.

A particular value for $R^2$ is one selected from $-L^{2A}-Q^{2A}$, $-NH-CO-Q^{2B}$, $-NR^v-CO-X-Q^{2C}$, $-NR^v-CS-Y-Q^{2C}$, and $-NH-CO-Q^{2D}$.

One particular compound of formula I is a pyridine in which one of $A^3$, $A^4$, $A^5$ and $A^6$ is N, and each of the others is $CR^3$, $CR^4$, $CR^5$ or $CR^6$, respectively.

Another particular compound of formula I is a thiophene in which the two adjacent residues $A^5$ and $A^6$ together form S, and $A^3$ and $A^4$ are $CR^3$ and $CR^4$, respectively.

Another particular compound of formula I is an indole in which the two adjacent residues $A^5$ and $A^6$ together form —NH—, and $A^3$ and $A^4$ together form a fused benz ring.

A further particular compound of formula I is a pyridine of formula Ia

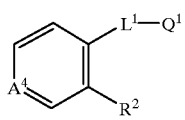

Ia wherein $A^4$ is N, and $L^1$, $Q^1$ and $R^2$ have any of the values defined herein.

A particular value for $Q^1$ is 4-methoxyphenyl.

A particular value for $R^2$ is, for example, (4-t-butylbenzoyl)amino, (4-methoxybenzoyl)amino, [4-(4-pyridyl)-benzoyl]amino or [1-(4-pyridyl)piperidin-4-yl]methoxycarbonylamino.

One particular compound of formula I as described herein is one in which $L^1-Q^1$ is $-NH-CO-Q^1$.

Another particular compound of formula I as described herein is one in which $L^1-Q^1$ is $-CO-NH-Q^1$.

A prodrug of a compound of formula I may be one formed in a conventional manner with a functional group of the compound, such as with an amino, hydroxy or carboxy group.

A compound of formula I may be prepared by processes which include processes known in the chemical art for the production of any known compounds of formula I or of structurally analogous compounds or by a novel process described herein. A process for the preparation of a novel compound of formula I (or a pharmaceutically acceptable salt thereof), novel processes for the preparation of a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a novel compound of formula I (or a pharmaceutically acceptable salt thereof) as provided in any of the above descriptions which is selected from any of those described in the examples, including the following.

(A) For a compound of formula I in which the linkage of $R^2$ to the ring terminates in $-NH-CO-$, $-NR^v-CO-$ or $-NR^v-CS-$, acylating an amine of formula II,

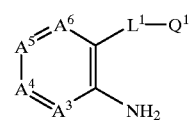

II or a corresponding amine in which the nitrogen bears the group $R^v$, using a corresponding acid which terminates with the group HO—CO— or HO—CS—, or an activated derivative thereof. Typical activated derivatives include the acid halides, activated esters, including 4-nitrophenyl esters and those derived from coupling reagents, as well as (when the product is a urea or thiourea) isocyanates and isothiocyanates. It may be preferred to deprotonate the amine using a strong base in anhydrous conditions for the acylation reaction, for example as described in Example 2, Part C.

(B) For a compound of formula I in which $-L^1-Q^1$ is $-NH-CO-Q^1$, acylating an amine of formula III

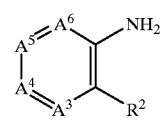

III using an acid of formula $HO-CO-Q^1$, or an activated derivative thereof. The conditions used may be similar to those of process (A), above.

(C) For a compound of formula I in which $-L^1-Q^1$ is $-CO-NH-Q^1$ and $R^2$ is of the form $-NH-CO-Q^2$, acylating an amine of formula $H_2N-Q^1$ using a [1,3] oxazine of formula IV,

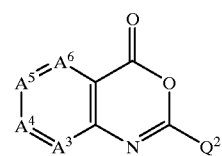

IV wherein $Q^2$ represents, for example, $Q^{2B}$, $Q^{2C}$ or $Q^{2D}$.

(D) For a compound of formula I in which $R^2$ is $-L^{2A}-Q^{2A}$ and D is carbonyl, diacylating a compound of formula II using an anhydride of formula V.

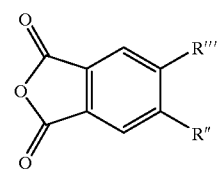

V

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

A novel intermediate or starting material compound such as, for example, a novel compound of formula II, III or IV, etc., provides a further aspect of the invention.

As mentioned above, a compound corresponding to a compound of formula I but in which a functional group is protected may serve as an intermediate for a compound of formula I. Accordingly, such a protected intermediate for a novel compound of formula I provides a further aspect of the invention. Protecting groups are well known in the art, for example as described in T. W. Greene and P. G. M. Wuts, "Protecting Groups in Organic Synthesis" (1991). Further, the protecting group may be a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of formula I which bears an acidic moiety, such as a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II, III, IV or VI discussed above.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary, e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 +mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
|---|---|
| Active ingredient | 250 |
| Starch, dried | 200 |

-continued

| | Quantity (mg/capsule) |
|---|---|
| Magnesium stearate | 10 |
| Total | 460 mg |

Formulation 2: A tablet is prepared using the ingredients below:

| | Quantity (mg/tablet) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

| | Weight |
|---|---|
| Active ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 +mL per minute.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

Enzyme+I⇌Enzyme-I $$Kass = \frac{[Enzyme - I]}{[(Enzyme) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 µL buffer (0.03 M Tris, 0.15 M NaCl pH 7) in each well, followed by 25 µL of inhibitor solution (in 100% methanol, or in 50% v:v aqueous methanol) and 25 µL enzyme solution; within two minutes, 150 µL aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA; 5.9 nM human thrombin or 1.4 nM bovine trypsin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.81 mM HD-Ile-Pro-Arg-pNA; and 0.37 nM urokinase is used with 0.30 mM pyro-gfsGlu-Gly-Arg-pNA.

Kass is calculated for a range of concentrations of test compounds and the mean value reported in units of liter per mole. In general, a factor Xa inhibiting compound of formula I of the instant invention exhibits a Kass of 0.1 to $0.5 \times 10^6$ L/mole or much greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 µL thrombin (73 NIH unit/mL) to 100 µL human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 µg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

FeCl$_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 µL is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varion) cartridges for sample preparation and a methanol/30 nM ammonium acetate buffer (pH 4) gradient optimized for each compound. % Oral bioavailability is calculated by the following equation:

$$\%\text{Oral bioavailabilty} = \frac{AUC\ po}{AUC\ iv} \times \frac{\text{Dose}\ iv}{\text{Dose}\ po} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, V$_D$; time of maximum plasma test compound concentration, Tmax; maximum concentration of test compound of Tmax, Cmax; plasma half-life, to 0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood PO$_2$, PCO$_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment. All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
aq=aqueous
Bn or Bzl=benzyl
Boc=t-butyloxycarbonyl
Bu=butyl
n-BuLi=butyllithium
Calc=calculated
conc=concentrated
DCC=dicyclohexylcarbodiimide
DMAP=4-dimethylaminopyridine
DMF=dimethylformamide
DMSO=dimethylsulfoxide
EDC=1-(3-dimethylaminopropyl)-3-ethylcarbodiimide hydrochloride
eq=(molar) equivalent
Et=ethyl
EtOAc=ethyl acetate
Et$_3$N=triethylamine
Et$_2$O=diethyl ether
EtOH=ethanol
FAB=Fast Atom Bombardment (Mass Spectroscopy)
Hex=hexanes
HOAt=1-hydroxy-7-azabenzotriazole
HOBT=1-hydroxybenzotriazole
HPLC=High Performance Liquid Chromatography
HRMS=high resolution mass spectrum
i-PrOH=isopropanol
IR=Infrared Spectrum
Me=methyl
MeI=methyl iodide
MeOH=methanol
MS-FD=field desorption mass spectrum
NBS=N-bromosuccinimide
NMR=Nuclear Magnetic Resonance
Ph=phenyl
i-Pr=isopropyl
RPHPLC=Reversed Phase High Performance Liquid Chromatography
satd=saturated
SiO$_2$=silica gel
TBS=tert-butyldimethylsilyl
TFA=trifluoroacetic acid THF=tetrahydrofuran
TIPS=triisopropylsilyl
TLC=thin layer chromatography
tosyl=p-toluenesulfonyl
triflic acid=trifluoromethanesulfonic acid Unless otherwise stated, pH adjustments and work up are with aqueous acid or base solutions. $^1$H-NMR indicates a satisfactory NMR spectrum was obtained for the compound described. IR indicates a satisfactory infra red spectrum was obtained for the compound described.

For consistency and clarity, a number of compounds are named as substituted diamine deriviatives.

EXAMPLE 1

Preparation of 3-(4-tert-butylbenzoyl)amino-N-(4-methoxyphenyl)-2-thiophenecarboxamide

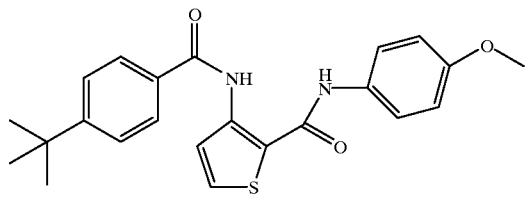

A. methyl 3-(4-tert-butylbenzoyl)amino-2-thiophene-carboxylate

A solution of methyl 3-amino-2-thiophenecarboxylate (400 mg, 2.54 mmol) and pyridine (0.226 mL, 2.80 mmol) in methylene chloride (12 mL) was treated with 4-tert-butylbenzoyl chloride (0.500 mL, 2.54 mmol). After consumption of the starting material, the mixture was concentrated in vacuo and the residue dissolved in ethyl acetate and water. The organic layer was washed once with water, once with saturated sodium chloride solution, dried (magnesium sulfate), and filtered. Concentration and purification of the residue by flash chromatography (silica gel, hexanes/ethyl acetate) yielded 689 mg (85%) of the title compound.

$^1$H-NMR, IR
MS-FD m/e 317 (M+)
Analysis for $C_{17}H_{19}NO_3S$.

| Calc: | C, 64.33; | H, 6.03; | N, 4.42. |
| Found: | C, 64.39; | H, 5.98; | N, 4.46. |

B. 3-(4-tert-butylbenzoyl)amino-2-thiophenecarboxylic Acid

A solution of methyl 3-(4-tert-butylbenzol)amindo-2-thiophenecarboxylate (9.67 g, 30 mmol) in 1,4-dioxane (75 mL) was treated with 2 N aqueous sodium hydroxide (75 mL). After 16 h, the mixture was treated with 5 N aqueous hydrochloric acid until the pH was ~2. The mixture was poured into ethyl acetate and the layers separated. The aqueous layer was washed three times with ethyl acetate and the combined extracts were dried (magnesium sulfate), filtered, and concentrated in vacuo to yield 8.09 g (89%) of the title compound.

$^1$H-NMR, IR
MS-FD m/e 303 (M+)
Analysis for $C_{16}H_{17}NO_3S$.

| Calc: | C, 63.34; | H, 5.65; | N, 4.62. |
| Found: | C, 63.56; | H, 5.93; | N, 4.32. |

C. 2-[4-(tert-butyl)phenyl]-4-oxo-4H-thieno[3,2-d]-[1.3]oxazine

A solution of 3-(4-tert-butylbenzoyl)amino-2-thiophenecarboxylic acid (8.1 g, 27 mmol) in methylene chloride (135 mL) was treated with oxalyl chloride (11.8 mL, 135 mmol). The mixture was slowly heated to afford a homogeneous solution. After 2 h, the mixture was concentrated in vacuo and the residue dissolved in methylene chloride (135 mL) and treated with pyridine (2.2 mL). After 1 hr, the mixture was concentrated in vacuo and the residue partitioned between ethyl acetate and water. The organic layer was washed four times with water, once with saturated sodium chloride solution, dried (magnesium sulfate), and filtered. Concentration and purification of the residue by flash chromatography (silica gel, hexanes/ethyl acetate) yielded 7.44 g (96%) of the title compound.

$^1$NMR, IR
MS-PD m/e 285 (M+)
Analysis for $C_{16}H_{15}NO_2S$.

| Calc: | C, 67.34; H, 5.30; N, 4.91. |
| Found: | C, 67.51; H, 5.56; N, 4.76. |

D. 3-(4-tert-butylbenzoyl)amino-N-(4-methoxyphenyl)-2-thiophenecarboxamide

A solution of 2-[4-(tert-butyl)phenyl]-4-oxo-4H-thieno[3,2-d][1.3]oxazine (60 mg, 0.21 mmol) and p-anisidine (26 mg, 0.21 mmol) in toluene (1 mL) was treated with p-toluenesulfonic acid (4 mg) and the resulting mixture heated at relux for 30 h. The mixture was concentrated in vacuo and the residue was purified by flash chromatography (silica gel, hexanes/ethyl acetate) to yield 35 mg (41%) of the title compound.

$^1$H-NMR
MS-FD m/e 408 (M+)
Analysis for $C_{23}H_{24}N_2O_3S$.

| Calc: | C, 67.62; H, 5.92; N, 6.86. |
| Found: | C, 67.79; H, 5.84; N, 6.77. |

EXAMPLE 2

Preparation of $N^3$-(4-tert-butylbenzoyl)-$N^2$-(4-methoxybenzoyl)-2,3-pyridinediamine

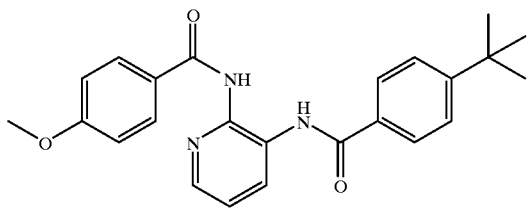

A. N³-(tert-butoxycarbonyl)-N²-(4-methoxybenzoyl)-2,3-pyridinediamine

A solution of N³-(tert-butoxycarbonyl)-2,3-pyridinediamine (446 mg, 2.13 mmol) in tetrahydrofuran (7 mL) was treated with potassium hexamethyldisilazide (894 mg, 4.48 mmol). After 0.1 hr, the mixture was treated with p-anisoyl chloride (0.365 mL, 2.13 mmol). After 0.5 hr, the mixture was poured into aqueous ammonium chloride solution and ethyl acetate. The organic layer was washed three times with water, once with saturated sodium chloride solution, dried (magnesium sulfate), and filtered. Concentration in vacuo and purification of the residue by flash chromatography (silica gel, hexanes/ethyl acetate) yielded 250 mg (34%) of the title compound.

$^1$H-NMR

B. N²-(4-methoxybenzoyl)-2,3-pyridinediamine

A solution of N³-(tert-butoxycarbonyl)-N²-(4-methoxybenzoyl)-2,3-pyridinediamine (350 mg, 1.02 mmol) in acetic acid (2 mL) at 0° C. was treated with boron trifluoride etherate (0.50 mL, 4.1 mmol). After 2 h, the mixture was poured into aqueous sodium bicarbonate and ethyl acetate. The aqueous layer was extracted three times with ethyl acetate and the combined extracts were dried (magnesium sulfate), filtered, and concentrated in vacuo. Purification of the residue by chromatography (silica gel, ethyl acetate/methylene chloride) yielded 122 mg (49%) of the title compound.

$^1$H-NMR

C. N³-(4-tert-butylbenzoyl)-N²-(4-methoxybenzoyl)-2,3-pyridinediamine

A solution of N²-(4-methoxybenzoyl)-2,3-pyridinediamine (92 mg, 0.38 mmol) in tetrahydrofuran (1 mL) was treated with potassium hexamethyldisilazide (160 mg, 0.80 mmol). After 0.25 hr, the mixture was treated with 4-tert-butylbenzoyl chloride. After 0.75 hr, the mixture was poured into a mixture of aqueous ammonium chloride solution and ethyl acetate. The organic layer was washed twice with water, once with saturated sodium chloride solution, dried (magnesium sulfate), and filtered. Concentration in vacuo and purification of the residue by flash cromatography (silica gel, methylene chloride/ethyl acetate) followed by recrystallization from ethyl acetate/hexanes yielded 31 mg (20%) of the title compound.

$^1$H-NMR
MS-FD m/e 403 (M+)
Analysis for $C_{24}H_{25}N_3O_3$.

| | |
|---|---|
| Calc: | C, 71.44; H, 6.24; N, 10.41. |
| Found: | C, 71.28; H, 6.33; N, 10.52. |

EXAMPLE 3

Preparation of N⁴-(4-tert-butylbenzoyl)-N³-(4-methoxy-benzoyl)-3,4-pyridinediamine

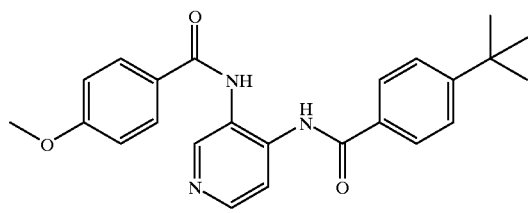

A. N⁴-(tert-butyloxycarbonyl)-3,4-pyridinediamine

A solution of 3,4-pyridinediamine (930 mg, 8.52 mmol) in tetrahydrofuran (20 mL) was treated with water (20 mL) and potassium carbonate (2.35 g, 17.0 mmol) followed by di-tert-butyl dicarbonate (1.86 g, 8.52 mmol). After 0.75 hr, the mixture was poured into a mixture of ethyl acetate and water. The aqueous layer was saturated with sodium chloride and extracted several times with ethyl acetate. The combined organic extracts were washed with saturated sodium chloride solution, dried (magnesium sulfate), and filtered. Concentration in vacuo and recrystallization from hexanes/ethyl acetate yielded 950 mg (53%) of the title compound.

$^1$H-NMR, IR

MS-FD m/e 209 (M+)

Analysis for $C_{10}H_{15}N_3O_2$.

| | |
|---|---|
| Calc: | C, 57.40; H, 7.23; N, 20.08. |
| Found: | C, 57.36; H, 7.19; N, 20.29. |

B. N⁴-(tert-butyloxycarbonyl)-N³-(4-methoxybenzoyl)-3,4-pyridinediamine

A solution of N⁴-(tert-butyloxycarbonyl)-3,4-pyridinediamine (500 mg, 2.40 mmol) and pyridine (0.213 mL, 2.63 mmol) in methylene chloride (12 mL) was treated with p-anisoyl chloride (408 mg, 2.40 mmol). After 0.75 hr, the mixture was poured into a mixture of ethyl acetate and 1 N aqueous sodium hydroxide. The organic layer was washed with saturated sodium chloride, dried (magnesium sulfate), and filtered. Concentration in vacuo and recrystallization of the residue, followed by flash chromatography (silica gel, hexanes/ethyl acetate) yielded 500 mg (60%) of the title compound.

1H-NMR, IR

MS-FD m/e 343 (M+)

Analysis for $C_{18}H_{21}N_3O_4$.

| | |
|---|---|
| Calc: | C, 62.96; H, 6.16; N, 12.24. |
| Found: | C, 62.18; H, 6.06; N, 11.68. |

C. N³-(4-methoxybenzoyl)-3,4-pyridinediamine

A solution of N⁴-(tert-butyloxycarbonyl)-N³-(4-methoxybenzoyl)-3,4-pyridinediamine (600 mg, 1.75 mmol) in methylene chloride (8 mL) was treated with trifluoroacetic acid (1.35 mL, 17.5 mmol). After 6.5 h, the mixture was concentrated and the residue dissolved in water and treated with 5 N aqueous sodium hydroxide. The resulting precipitate was collected by filtration yielding 325 mg (76%) of the title compound.

$^1$H-NMR, IR

MS-FD m/e 243 (M+)

Analysis for $C_{13}H_{13}N_3O_2$.

| Calc: | C, 64.19; H, 5.39; N, 17.27. |
| Found: | C, 63.92; H, 5.28; N, 17.15. |

D. $N^4$-(4-tert-butylbenzoyl)-$N^3$-(4-methoxybenzoyl)-3,4-pyridinediamine

Using 4-tert-butylbenzoyl chloride and a similar procedure to that described for Example 2, Part C, $N^3$-(4-methoxybenzoyl)-3,4-pyridinediamine (300 mg, 1.23 mmol) yielded 243 mg (49%) of the title compound.
$^1$H-NMR, IR
MS-FD m/e 403 (M+)
Analysis for $C_{24}H_{25}N_3O_3$.

| Calc: | C, 71.44; H, 6.25; N, 10.41. |
| Found: | C, 71.28; H, 6.16; N, 10.28. |

EXAMPLE 4

Preparation of $N^3$-(4-tert-butylbenzoyl)-$N^4$-(4-methoxy-benzoyl)-3,4-pyridinediamine

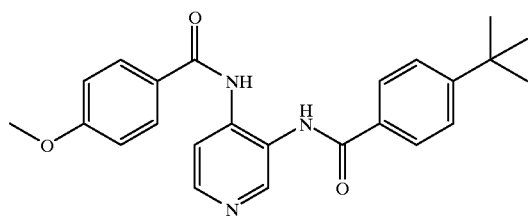

A. $N^3$-(4-tert-butylbenzoyl)-$N^4$-(tert-butyloxycarbonyl)-3,4-pyridinediamine Using a similar procedure to that described for Example 3, Part B, $N^4$-(tert-butyloxycarbonyl)-3,4-pyridinediamine (450 mg, 2.15 mmol) yielded 516 mg (65%) of the title compound.
$^1$H-NMR, IR
MS-FD m/e 369 (M+)
Analysis for $C_{21}H_{27}N_3O_3$.

| Calc: | C, 68.27; H, 7.37; N, 11.37. |
| Found: | C, 68.46; H, 7.38; N, 11.19. |

B. $N^3$-(4-tert-butylbenzoyl)-3,4-pyridinediamine

Using a similar procedure to that described for Example 3, Part C, $N^3$-(4-tert-butylbenzoyl)-$N^4$-(tert-butyloxycarbonyl)-3,4-pyridinediamine (516 mg, 1.40 mmol) yielded 324 mg (86%) of the title compound.
$^1$H-NMR, IR
MS-FD m/e 269 (M+)
Analysis for $C_{16}H_{19}N_3O$.

| Calc: | C, 71.35; H, 7.11; N, 15.60. |
| Found: | C, 71.01; H, 7.06; N, 14.90. |

C. $N^3$-(4-tert-butylbenzoyl)-$N^4$-(4-methoxybenzoyl)-3,4-pyridinediamine

A solution of $N^3$-(4-tert-butylbenzoyl)-3,4-pyridinediamine (400 mg, 1.49 mmol), pyridine (0.264 mL), and p-anisoyl chloride (0.254 mL, 1.49 mmol) in toluene (12 mL) was heated at reflux for 3 h. The mixture was filtered and the filtrate poured into a mixture of ethyl acetate and water. The organic layer was washed three times with water, once with saturated sodium chloride solution, dried, and filtered. Concentration in vacuo and purification of the residue by recrystallization (methanol/ethyl acetate/hexanes) followed by flash chromatography (silica gel, ethyl acetate/methylene chloride) yielded 75 mg (13%) of the title compound.
$^1$H-NMR, IR
NS-FD m/e 403 (M+)
Analysis for $C_{24}H_{25}N_3O_3$.

| Calc: | C, 71.44; H, 6.24; N, 10.41. |
| Found: | C, 69.90; H, 5.95; N, 10.25. |

EXAMPLE 5

Preparation of $N^2$-(4-tert-butylbenzoyl)-$N^3$-(4-metboxy-benzoyl)-2,3-pyridinediamine

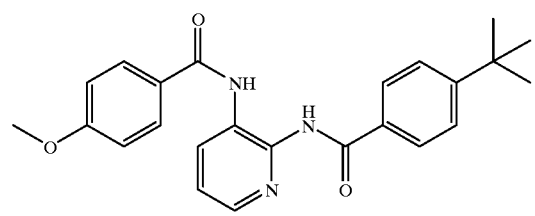

A. $N^2$-(4-tert-butylbenzoyl)-2,3-pyridinediamine

Using a similar procedure to that described for Example 3, Part B, $N^3$-(tert-butyloxycarbonyl)-2,3-pyridinediamine (1.00 g, 4.78 mmol) yielded $N^2$-(4-tert-butylbenzoyl)-$N^3$-(tert-butyloxycarbonyl)-2,3-pyridinediamine (894 mg). Using a similar procedure to that described for Example 2, Part B, this crude material yielded 400 mg (31%) of the title compound.

$^1$H-NMR

B. $N^2$-(4-tert-butylbenzoyl)-$N^3$-(4-methoxybenzoyl)-2,3-pyridinediamine

Using a similar procedure to that described for Example 3, Part C, $N^2$-(4-tert-butylbenzoyl)-2,3-pyridinediamine (80 mg, 0.30 mmol) yielded 28 mg (23%) of the title compound.

$^1$H-NMR

MS-FD m/e 403 (M+)

Analysis for $C_{24}H_{25}N_3O_3$.

| Calc: | C, 71.44; | H, 6.25; | N, 10.41. |
| Found: | C, 71.51; | H, 6.28; | N, 10.31. |

EXAMPLE 6

Preparation of $N^4$-(4-methoxybenzoyl)-$N^3$-[4-(4-pyridyl)benzoyl]-3,4-pyridinediamine.

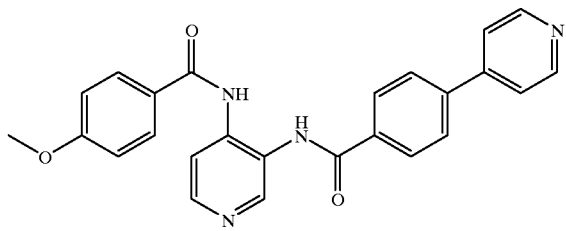

A. sodium 4-(4-pyridyl)benzoate

A solution of 4-chloropyridine hydrochloride (3.00 g, 20.0 mmol), 4-carboxybenzeneboronic acid (4.97 g, 30.0 mmol), 1 M aqueous sodium carbonate solution (50 mL), 1,4-bis(diphenylphosphino)butane palladium(II) dichloride (300 mg, 0.70 mmol), and ethanol (10 mL) in toluene (40 mL) was heated at reflux for 16 h. The mixture was diluted with methanol and filtered through diatomaceous earth. The filtrate was concentrated in vacuo and the pH was adjusted to 14 by the addition of 1 N aqueous sodium hydroxide. After heating the filtrate to boiling, the insoluble material was removed by filtration, and the resulting filtrate was allowed to cool to room temperature. The resulting precipitate was collected by filtration to yield 1.83 g (41%) of the title compound.
$^1$H-NMR B. $N^4$-(tert-butyloxycarbonyl)-$N^3$-[4-(4-pyridyl)benzoyl]-3,4-pyridinediamine A suspension of sodium 4-(4-pyridyl)benzoate (425 mg, 1.92 mmol) in methylene chloride was treated with oxalyl chloride (0.840 mL, 9.60 mmol), followed by dimethylformamide (0.01 mL). After 0.75 h, the mixture was concentrated in vacuo. The residue was then dissolved in methylene chloride and added dropwise to a solution of $N^4$-(tert-butyloxycarbonyl)-3,4-pyridinediamine (400 mg, 1.92 mmol) and pyridine (0.31 mL) in methylene chloride (2 mL) and tetrahydrofuran (1 mL). After 16 h, the mixture was poured into ethyl acetate and 1 N aqueous sodium hydroxide. The organic layer was washed once with 1 N aqueous sodium hydroxide, once with saturated sodium chloride solution, dried (potassium carbonate), and filtered. The residue was purified by flash chromatography (silica gel, ethyl acetate/hexanes) to yield 75 mg (10%) of the title compound.
$^1$H-NMR, IR
MS-FD m/e 390 (M+)
Analysis for $C_{22}H_{22}N_4O_3$.

| Calc: | C, 67.68; | H, 5.68; | N, 14.35. |
| Found: | C, 66.95; | H, 6.03; | N, 13.67. |

C. $N^3$-[4-(4-pyridyl)benzoyl]-3,4-pyridinediamine

Using a similar procedure to that described for Example 2, Part B, $N^4$-(tert-butyloxycarbonyl)-$N^3$-[4-(4-pyridyl)benzoyl]-3,4-pyridinediamine (95 mg, 0.23 mmol) yielded 55 mg (82%) of the title compound.
$^1$H-NMR D. $N^4$-(4-methoxybenzoyl)-$N^3$-[4-(4-pyridyl)benzoyl]-3,4-pyridinediamine Using 4-methoxybenzoyl chloride and a similar procedure to that described for Example 2, Part C, $N^3$-[4-(4-pyridyl)-benzoyl]-3,4-pyridinediamine (55 mg, 0.19 mmol) yielded 3.2 mg (4%) of the title compound.
$^1$H-NMR MS-FD m/e 424 (M+)

EXAMPLES 7–9

The following procedure was use in Examples 7–9:

To a small glass vial with a Teflon lined cap was added a 1,2-diamino aromatic compound (about 0.25 mmol) in tetrahydrofuran (3 mL), followed by poly(4-vinylpyridine) (250 mg, 1 mmol) and p-anisoyl chloride (0.625 mmol). After agitating this mixture for 24 h on a platform shaker, aminomethylated polystyrene (1 g, 1 mmol) was added and agitation continued for another 8 h. The solution was filtered and concentrated in vacuo, and the residue triturated with diethyl ether. The resulting solid was filtered and dried in vacuo to give approximately 50 mg of the title compound.

EXAMPLE 7

5-Bromo-6-methyl-$N^2$,$N^3$-bis(4-methoxybenzoyl)-2,3-pyridinediamine

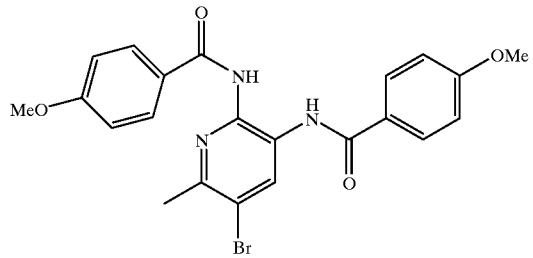

MS-FD m/e 471 (M+).

EXAMPLE 8

$N^3$,$N^4$-bis (4-Methoxybenzoyl)-3,4-pyridinediamine

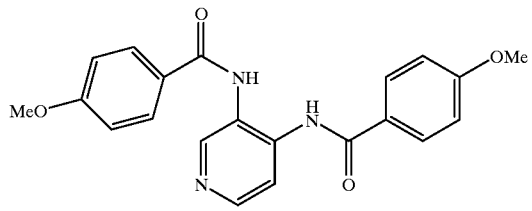

MS-FD m/e 377 (M+).

EXAMPLE 9

$N^2,N^3$-bis (4-Methoxybenzoyl)-2,3-pyridinediamine

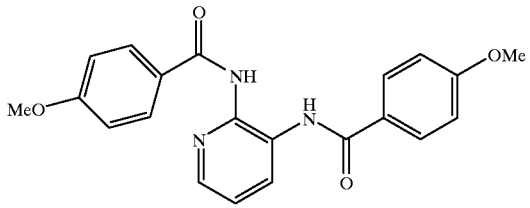

MS-FD m/e 377 (M+).

EXAMPLE 10

Preparation of 3-(4-Methoxybenzoyl)amino-N-(4-methoxyphenyl)-2-indolecarboxamide

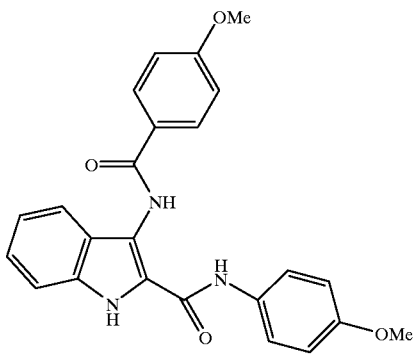

A. 3-(4-methoxybenzoyl)amino-2-indolecarboxylic Acid Ethyl Ester

To a solution of 3-amino-2-indolecarboxylic acid ethyl ester (500 mg, 2.45 mmol) and triethylamine (272 mg, 2.70 mmol) in methylene chloride (5 mL) was added anisoyl chloride (418 mg, 2.45 mmol). The resulting mixture was stirred for 18 h at room temperature. The reaction mixture was diluted with ethyl acetate and washed with water. The organic phase was washed with 1 N aqueous hydrochloric acid, dried (sodium sulfate), filtered, and concentrated in vacuo to provide a yellow solid. Recrystallization from hexane/ethyl acetate provided 780 mg (94%) of the title compound as a yellow solid.
$^1$H-NMR, IR
MS-FD m/e 338 (M+)
Analysis for $C_{19}H_{18}N_2O_4$.

| Calc: | C, 67.44; | H, 5.36; | N, 8.28. |
|---|---|---|---|
| Found: | C, 67.46; | H, 5.35; | N, 8.16. |

B. 3-(4-methoxybenzoyl)amino-2-indolecarboxylic Acid

To a solution of 3-(4-methoxybenzoyl)amino-2-indolecarboxylic acid ethyl ester (720 mg, 2.13 mmol) in tetrahydrofuran (7 mL) was added 5 N aqueous sodium hydroxide (2 mL). The resulting mixture was stirred for 10 h at room temperature. An additional portion of 5 N aqueous sodium hydroxide (5 mL) was added and the mixture heated at 60° C. for 5 h. The mixture was cooled to room temperature, stirred for 10 h, diluted with water, and extracted with diethyl ether. The aqueous layer was acidified with concentrated hydrochloric acid and extracted with three fresh portions of ethyl acetate. The combined ethyl acetate fractions were dried (sodium sulfate), filtered, and concentrated in vacuo to provide 450 mg (68%) of the title compound as a yellow solid.
$^1$H-NMR, IR
MS-FD m/e 310 (M+)
Analysis for $C_{17}H_{14}N_2O_4$.

| Calc: | C, 65.80; | H, 4.55; | N, 9.03. |
|---|---|---|---|
| Found: | C, 64.70; | H, 4.66; | N, 8.59. |

C. 3-(4-methoxybenzoyl)amino-N-(4-methoxyphenyl)-2-indolecarboxamide

To a solution p-anisidine (79 mg, 0.645 mmol) in methylene chloride (5 mL) was added 3-(4-methoxybenzoyl)amino-2-indolecarboxylic acid (200 mg, 0.645 mmol), 1-(3-dimethylaminopropyl)-3-ethylcarbodiimide hydrochloride (247 mg, 1.29 mmol), and 4-dimethylaminopyridine (8.0 mg, 0.065 mmol). The resulting solution was stirred at room temperature for 6 h. The resulting precipitate was collected via vacuum filtration to provide 38 mg (14%) of the title compound as a white solid.
$^1$H-NMR, IR
MS-FD m/e 415 (M+)
Analysis for $C_{24}H_{21}N_3O_4$.

| Calc: | C, 69.39; | H, 5.10; | N, 10.11. |
|---|---|---|---|
| Found: | C, 68.68; | H, 4.96; | N, 10.15. |

EXAMPLE 11

Preparation of $N^4$-[(4-Dimethylamino)benzoyl]-$N^3$-(4-methoxybenzoyl)-3,4-pyridinediamine

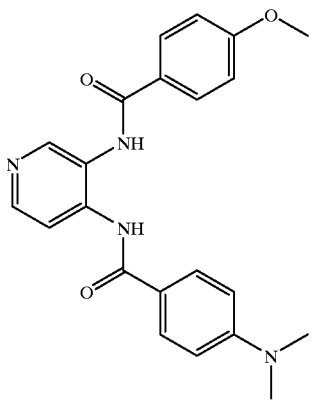

A. 4-(Dimethylamino)benzoyl Chloride

A solution of 4-(dimethylamino)benzoic acid and thionyl chloride in methylene chloride was refluxed 4 h. Volatile solvents were removed in vacuo to yield 1.10 g of 4-(dimethylamino)benzoyl chloride. This material was used in subsequent reactions without purification.

B. $N^4$-[(4-Dimethylamino)benzoyl]-$N^3$-(4-methoxybenzoyl)-3,4-pyridinediamine.

To a solution of $N^3$-(4-methoxybenzoyl)-3,4-pyridinediamine (193 mg, 0.79 mmol) and 4-(dimethylamino)benzoyl chloride (183 mg, 1.00 mmol) in 5 mL methylene chloride was added 0.5 mL pyridine and a catalytic amount of 4-dimethylaminopyridine. The mixture was stirred 16 h at ambient temperature under nitrogen then partitioned between methylene chloride and saturated sodium hydrogen carbonate solution. The organic portion was dried over magnesium sulfate and concentrated in vacuo. The residue was dissolved in ethyl acetate and hexane added until cloudy. The mixture was sonicated inducing crystallization. The solid was collected by filtration and dried under vacuum to yield 306 mg (99%) of the title compound.

MS, Ion spray, m/e: 391(p+1).

Analysis for $C_{22}H_{22}N_4O_3$.

| | | | |
|---|---|---|---|
| Calc. | C, 67.58; | H, 5.68; | N, 14.35. |
| Found: | C, 67.19; | H, 6.01; | N, 13.79. |

What is claimed is:

1. A compound of formula I wherein $A^3, A^4, A^5$ and $A^6$, together with the two carbons to which they are attached, complete a substituted indole ring in which $A^3$ and $A^4$ together form a fused benz ring, and $A^5$ and $A^6$ together form —NH—;

wherein $L^1$ is —CO—NH— such that —$L^1$—$Q^1$ is —CO—NH—$Q^1$;

$Q^1$ is phenyl, 2-furanyl, 2-thienyl, 4-thiazolyl, 2-pyridyl, 2-naphthyl, 1,2-dihydrobenzofuran-5-yl, 1,2-dihydrobenzofuran-6-yl or 1,2-benzisoxazol-6-yl in which the phenyl may bear a 2-fluoro substituent or may bear one, two or three substituents at the 3-, 4- or 5-position(s) independently selected from halo, cyano, carbamoyl, aminomethyl, methyl, methoxy, difluoromethoxy, hydroxymethyl, formyl, vinyl, amino, hydroxy and 3,4-methylenedioxy, the 2-furanyl or 2-thienyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position; or —CO—$Q^1$ is cyclopentenylcarbonyl or cyclohexenylcarbonyl;

$R^2$ is —$L^{2A}$—$Q^{2A}$, —$L^{2B}$—$Q^{2B}$, —$L^{2C}$—$Q^{2C}$ or —$L^{2D}$—$Q^{2D}$ wherein $L^{2A}$ is a direct bond; and $Q^{2A}$ is in which D is carbonyl or —$CHR^k$— in which $R^k$ is hydrogen, hydroxy, (1–6C)alkoxy or —$CH_2$—$R^j$ in which $R^j$ is carboxy, [(1–4C)alkoxy]carbonyl or carbamoyl which may bear one or two (1–2C)alkyl substituents on the nitrogen; and one of $R^m$ and $R^n$ is hydrogen and the other is amino, bromo, (1–4C)alkyl or (1–4C)alkoxy, or $R^m$ and $R^n$ together form a benz ring;

$L^{2B}$ is —NH—CO— such that —$L^{2B}$—$Q^{2B}$ is —NH—CO—$Q^{2B}$; and $Q^{2B}$ is in which $R^o$ is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —$S(O)_q$— (wherein q is 0, 1 or 2), or —$NR^r$— (wherein $R^r$ is hydrogen or methyl); and $R^q$ is (1–6C)alkyl, phenyl, 3-pyridyl or 4-pyridyl;

$L^{2C}$ is —$NR^v$—CO—X— or —$NR^v$—CS—Y— such that —$L^{2C}$—$Q^{2C}$ is —$NR^v$—CO—X—$Q^{2C}$ or —$NR^v$—CS—Y—$Q^{2C}$ in which X is —$(CH_2)_x$— (wherein x is 0, 1 or 2), —$NR^w$—, $NR^w$—$CH_2$—, —O—, —O—$CH_2$— or —S—$CH_2$—; Y is —$NR^w$—$CH_2$— or —O—$CH_2$—; and each of $R^v$ and $R^w$ is independently hydrogen, benzyl or (1–6C)alkyl which is not branched at the α-position; and $Q^{2C}$ is 1-(4-pyridyl)piperidin-4-yl, 1-(4-pyridyl)piperidin-3-yl or 1-(4-pyridyl)pyrrolidin-3-yl in which the pyridyl may bear a substituent at its 2-position selected from cyano, aminomethyl, carboxy, hydroxymethyl and (1–2C) alkyl;

$L^{2D}$ is —NH—CO— such that —$L^{2D}$—$Q^{2D}$ is —NH—CO—$Q^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl or 3,4-didehydropiperidin-4-yl (either one bearing a substituent at the 1-position selected from methylsulfonyl, phenylsulfonyl, (1–5C) alkyl, (4–7C)cycloalkyl, tetrahydropyran-4-yl, 4-thiacyclohexyl and —$CH_2$—$R^z$ in which $R^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent);

or a prodrug of the compound of formula I;

or a pharmaceutically acceptable salt of the compound of formula I or prodrug thereof.

2. A method of inhibiting factor Xa in a mammal comprising administering to a mammal in need thereof, a factor Xa inhibiting amount of a compound of formula I

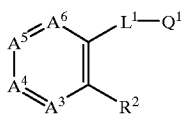

as claimed in claim 1.

3. The compound of claim 1 wherein
$A^3, A^4, A^5$ and $A^6$, together with the two carbons to which they are attached, complete a substituted indole ring in which $A^3$ and $A^4$ together form a fused benz ring, and $A^5$ and $A^6$ together form —NH—;
wherein
$L^1$ is —CO—NH— such that —$L^1$—$Q^1$ is —CO—NH—$Q^1$;
$Q^1$ is phenyl, 2-thienyl, 4-thiazolyl, 2-pyridyl, 2-naphthyl or 1,2-benzisoxazol-6-yl in which the phenyl may bear one, two or three substituents at the 3-, 4- or 5-position (s) independently selected from halo, cyano, carbamoyl, aminomethyl, methyl, methoxy, hydroxymethyl, formyl, vinyl, amino, hydroxy and 3,4-methylenedioxy, the 2-thienyl may bear a chloro or methyl substituent at the 5-position, the 4-thiazolyl may bear an amino substituent at the 2-position, the 2-pyridyl may bear an amino substituent at the 6-position, and the 1,2-benzisoxazol-6-yl may bear a chloro or methyl substituent at the 3-position;
$R^2$ is —$L^{2A}$—$Q^{2A}$, —$L^{2B}$—$Q^{2B}$, —$L^{2C}$—$Q^{2C}$ or —$L^{2D}$—$Q^{2D}$ wherein
$L^{2A}$ is a direct bond; and
$Q^{2A}$ is

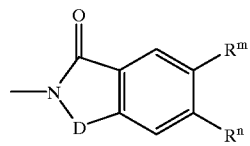

in which D is carbonyl or —$CHR^k$— in which $R^k$ is hydrogen, hydroxy, (1–6C)alkoxy or —$CH^2$—$R^j$ in which $R^j$ is carboxy, [(1–4C)alkoxy]carbonyl or carbamoyl which may bear one or two (1–2C)alkyl substituents on the nitrogen; and one of $R^m$ and $R^n$ is hydrogen and the other is amino, bromo, (1–4C)alkyl or (1–4C)alkoxy, or $R^m$ and $R^n$ together form a benz ring;
$L^{2B}$ is —NH—CO— such that —$L^{2B}$—$Q^{2B}$ is —NH—CO—$Q^{2B}$; and
$Q^{2B}$ is

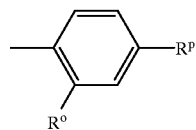

in which $R^o$ is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —$S(O)_q$— (wherein q is 0, 1 or 2), or —$NR^r$— (wherein $R^r$ is hydrogen or methyl); and $R^q$ is (1–6C)alkyl, phenyl, 3-pyridyl or 4-pyridyl;

$L^{2C}$ is —$NR^v$—CO—X— or $NR^v$—CS—Y— such that —$L^{2C}$—$Q^{2C}$ is —$NR^v$—CO—X—$Q^{2C}$ or —$NR^v$—CS—Y—$Q^{2C}$ in which X is —$(CH_2)_x$— (wherein x is 0, 1 or 2), —$NR^w$—$CH_2$—, —O—$CH_2$— or —S—$CH_2$—; Y is —$NR^w$—$CH_2$— or —O—$CH_2$—; and each of $R^v$ and $R^w$ is independently hydrogen, benzyl or (1–6C)alkyl which is not branched at the α-position; and $Q^{2C}$ is 1-(4-pyridyl)piperidin-4-yl in which the pyridyl may bear a substituent at its 2-position selected from cyano, aminomethyl, carboxy, hydroxymethyl and (1–2C)alkyl;

$L^{2D}$ is —NH—CO— such that —$L^{2D}$—$Q^{2D}$ is —NH—CO—$Q^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —$CH_2$—$R^z$ in which $R^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substituent;

or a prodrug of the compound of formula I;

or a pharmaceutically acceptable salt of the compound of formula I or prodrug thereof.

4. The compound of claim 1 wherein $Q^1$ is 4-methoxyphenyl.

5. The compound of claim 1 wherein $R^2$ is (4-t-butylbenzoyl) amino, (4-methoxybenzoyl) amino, [4-(4-pyridyl)benzoyl]amino or [1-(4-pyridyl)piperidin-4-yl] methoxycarbonylamino.

6. A pharmaceutical composition comprising a compound of formula I, or prodrug or pharmaceutically acceptable salt thereof, as claimed in claim 1 in association with a pharmaceutically acceptable carrier, excipient or diluent.

7. A process for preparing a compound of formula I (or a pharmaceutically acceptable salt thereof) as provided in claim 1 which is selected from (A) for a compound of formula I in which the linkage of $R^2$ to the ring terminates in —NH—CO—, —$NR^v$—CO— or —$NR^v$—CS—, acylating an amine of formula II,

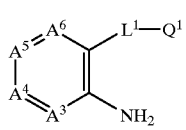

or a corresponding amine in which the nitrogen bears the group $R^v$, using a corresponding acid which terminates with the group HO—CO— or HO—CS—, or an activated derivative thereof;

(B) for a compound of formula I in which —$L^1$—$Q^1$ is —CO—NH—$Q^1$ and $R^2$ is of the form —NH—CO—$Q^2$, acylating an amine of formula $H_2N$—$Q^1$ using a [1,3]oxazine of formula IV,

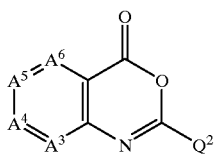

wherein $Q^2$ represents $Q^{2B}$, $Q^{2C}$ or $Q^{2D}$;

(C) for a compound of formula I in which $R^2$ is —$L^{2A}$—$Q^{2A}$ and D is carbonyl, diacylating a compound of formula II using an anhydride of formula V;

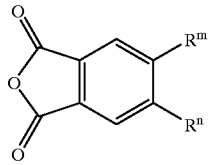

whereafter, for any of the above procedures when a functional group is protected using a protecting group, removing the protecting group;

whereafter for any of the above procedures, when a pharmaceutically acceptable salt of a compound of formula is required, it is obtained by reacting the basic form of basic compound of formula I with an acid affording a physiologicaly acceptable counterion or the acidic form of an acidic compound of formula I with a base affording a physiologically acceptable counterion or by any other conventional procedure; and wherein, unless otherwise specified, $L^1$, $Q^1$, $R^2$, $R^m$, $R^n$, $A^3$, $A^4$, $A^5$ and $A^6$ have any of the values defined in claim 1.

8. The compound of claim 2 wherein $Q^1$ is 4-methoxyphenyl.

9. The compound of claim 3 wherein $R^2$ is (4-t-butylbenzyl)amino, (4-methoxybenzoyl)amino, [4-(4-pyridyl)benzoyl]amino or [1-(4-pyridyl)piperidin-4-yl]methoxycarbonylamino.

10. The compound of claim 1 wherein $Q^1$ is 4-methoxyphenyl and $R^2$ is (4-t-butylbenzoyl)amino, (4-methoxybenzoyl)amino, [4-(4-pyridyl)benzoyl]amino or [1-(4-pyridyl)piperidin-4-yl]methoxycarbonylamino.

11. The compound of claim 1, 3, 4, 5, 8, or 9 wherein for an alkyl group or the alkyl portion of an alkyl containing group, (1–2C)alkyl is methyl or ethyl; (1–4C)alkyl is methyl, ethyl, propyl, isopropyl butyl, isobutyl, or t-butyl; (1–6C)alkyl is methyl, ethyl, propyl, butyl, pentyl or hexyl; and halo is bromo or chloro.

12. The compound of claim 11 wherein for an alkyl group or the alkyl portion of an alkyl containing group, (1–2C) alkyl is methyl; (1–4C)alkyl is methyl, isopropyl, butyl or t-butyl; (1–6C)alkyl is methyl, butyl or hexyl; and halo is chloro.

* * * * *